United States Patent
Tanzi

[11] Patent Number: 5,955,560
[45] Date of Patent: Sep. 21, 1999

[54] CHAIN EXTENDER FOR THE SYNTHESIS OF HEPARINIZABLE, BIOCOMPATIBLE POLYMERS

[75] Inventor: Maria Cristina Tanzi, Milan, Italy

[73] Assignee: Tecnobiomedica S.p.A., Pomezia, Italy

[21] Appl. No.: 09/055,981

[22] Filed: Apr. 7, 1998

[30] Foreign Application Priority Data

Apr. 8, 1997 [IT] Italy .................... MI97A0802

[51] Int. Cl.⁶ .................... C08G 18/10
[52] U.S. Cl. .................... 528/65; 528/73; 525/54.1; 525/54.2; 523/112; 514/822; 514/56; 427/414; 623/1
[58] Field of Search .................... 528/65, 73; 525/54.1, 525/54.2; 523/112; 514/822, 56; 427/414; 623/1

[56] References Cited

U.S. PATENT DOCUMENTS 4,448,905  5/1984  Lin et al. .................... 521/164
5,159,051  10/1992  Onwumere et al. .................... 528/67

OTHER PUBLICATIONS

R. Barbucci et al; Synthesis and Physicochemical Characterization of a New Material Based on Polyurethane; Biomaterials 10(5) pp. 299–308, 1989.
Chemical Abstracts, vol. 55, No. 7, Apr. 3, 1961, Abs. No. 6485b, S. Groszkowski, "New Derivatives of Piperazine", XP002072927; & Roczniki Chem., vol. 34, 1960, pp. 707–708.

*Primary Examiner*—Rachel Gorr
*Attorney, Agent, or Firm*—Griffin, Butler, Whisenhunt & Szipl, LLP

[57] ABSTRACT

The compound of formula

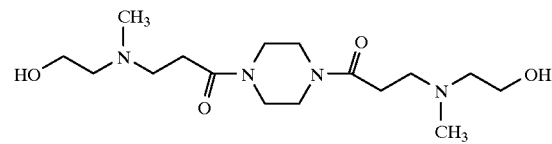

is useful as chain extender in the preparation of polymers, in particular of linear and cross-linkable, heparinizable, biocompatible polymers.

15 Claims, 3 Drawing Sheets

CHAIN EXTENDER FOR THE SYNTHESIS OF HEPARINIZABLE, BIOCOMPATIBLE POLYMERS

The present invention relates to heparinizable, biocompatible, elastomeric materials. In particular the present invention relates to a new chain extender that gives said materials the desired properties of heparin absorption, together with the necessary physico-chemical and mechanical characteristics typical of the biocompatible materials.

BACKGROUND OF THE INVENTION

The lack of a suitable hemocompatibility of elastomeric materials to be used in the preparation of cardio-vascular prostheses is the major problem to be solved in the study and application of prosthetic materials in the cardio-vascular field. The contact of an extraneous surface with blood always triggers coagulation mechanisms; as a consequence, a therapy with anticoagulants is combined with a prostheses implant, with a subsequent risk of onset of side effects, such as bleeding. The search for non thrombogenic surfaces is one of the means now under study for the resolution of the problem (T. Akutsu, Artificial Heart, Igaku Shoin Ltd., Tokyo, (1975); F. W. Hastings in Advances in Chemistry Series, ed R. F. Gould, (1987)), by means of biological activity (adhesiveness by stimulating the growth of endothelial cells) or biochemical (for example heparin release ability, through a controlled release mechanism, or keeping this anticoagulant molecule stably, without reducing its activity (M. C. Tanzi, B. Barzaghi, R. Anouchinsky, S. Bilenkis, A. Penhasi, D. Cohn "Grafting reactions and heparin adsorbtion of polyamidoamine-grafted polyurethane amides" Biomaterials, 13, 425–431 (1992)).

In order to avoid unwanted side effects, biocompatibility is a fundamental requirement of an extraneous material when the latter is contacted with human organism. On the other side, there are a great number of biomedical applications, which provide the use of synthetic polymers. These polymers can delay metabolism or excretion of drugs, which otherwise would require repeated or frequent administrations. The action of these polymers occurs through the formation of covalent bonds having controlled stability in biological environment, or, alternatively the polymers are the constituents of systems for the controlled release of drugs, by physical absorption and subsequent release. Prosthetic devices, among which vascular grafts made with synthetic polymers, have been used for more than 40 years; and now design and construction of artificial organs, such as heart, are at reach.

In the most part of the cases disclosed in the past literature, the bond between polymer and heparin was not established directly, but through preliminary adsorption of quaternary ammonium salts on the polymeric material and subsequent complex formation with heparin on the modified material.

This heparinization method showed several drawbacks, which made difficult its application in living organisms in the long period. In fact, ammonium salts tend to deadsorb; further, the compounds containing quaternary ammonium groups generally showed haemolytic activity and affected platelets.

Subsequent studies led to the discovery of polymers containing tertiary amino groups regularly distributed along the macromolecular chain. These last polymers, polyamidoamines (PAA) are capable of linking to heparin stably. Linear polymers of the polyamidoamine type, obtained by addition of polyaddition of primary monoamines or secondary diamines to bisacrylamides, have been widely disclosed in the past (F. Danusso, P. Ferruti, G. Ferroni, La Chimica and l'Industria, 49, 271, (1967); F. Danusso, P. Ferruti, G. Ferroni, La Chimica and l'Industria, 49, 453, (1967); F. Danusso, P. Ferruti, La Chimica and l'Industria) as compounds capable of complexing heparin stably (M. A. Marchisio, T. Longo, P. Ferruti, Experientia, 29, 93, (1973); P. Ferruti, E. Martuscelli, L. Nicolais, M. Palma, F. Riva, Polymer, 18, 387, (1977); P. Ferruti in (IUPAC) Polymeric amines and ammonium salts, E. J. Goethals Ed., Pergamon Press, Oxford and New York, 305–320, (1980); P. Ferruti, M. A. Marchisio, Biomedical and dental application of polymers, C. G. Gebelein and F. Koblitz Eds., Plenum Publ. Co., New York, 39–57, (1981)) and to assure a natural anticoagulant activity to the surfaces of the materials on which they were grafted or inserted (R. Barbucci et 25 al., Biomaterials, 10, 299–308, (1989); M. C. Tanzi, M. Levi, Journal of Biomedical Materials Research, 23, 863 (1989)).

Heparin is a mucopolysaccharide containing carbonyl and sulphonyl groups, which behaves as a polyanion in aqueous solution at physiological pH. The ability of PAA of giving stable bonds with heparin is due to the interaction of ionic and electrostatic type that occurs between the negative charges of heparin and the amino groups of the PAA, which are protonated at physiological pH. Accordingly, new materials have been obtained, wherein the polyamidoamino segments were linked to segments of conventional polymers (for example styrene) with the purpose of obtaining materials having good mechanical properties and physico-chemical characteristics such as to turn out to be, after to treatment with heparin, permanently non-thrombogenic, therefore usable for the manufacture of artificial prostheses.

The main drawback of PAA and similar polymers is due to non-uniformity of molecular weight and to the difficulty of obtaining terminal groups all of the same kind. Accordingly, PAA are not suitable for use as macromonomers in the reproducible synthesis of polymers.

Polyurethanes are polymeric materials containing the urethane group —NH—CO—O— in the macromolecular chain. These materials, according to their composition and structure, can exist in linear form (thermoplastic polyurethanes), cross-linked (thermosetting polyurethanes) and expanded (urethane foams).

Thermoplastic polyurethanes (Lilaoniktul, S. L. Cooper, "Properties of Thermoplastic Polyurethanes Elastomerics", Advances in Urethanes Sciences and Technology, K. C. Frisch, S L Reegen, 7) are linear copolymers of the —AnBm— type, wherein An (soft segments) are generally of the polyester, polyether or polyalkyldiol type, with a molecular weight ranging between 600 and 3000. Hard segments (Bm) are formed by the parts of the macromolecular chain deriving from the reaction of an aromatic or aliphatic diisocyanate with a diol or a low molecular weight diamine (chain extender).

Thermoplastic polyurethane elastomers are then formed by segments of two structural entities having different characteristics within the same polymeric chain. At working temperature, one of the two components has flexibility properties (soft segment), whereas the second unit has a rigid nature either glass or hemicrystalline (hard segment). Due to incompatibility between the two components, these materials are characterised by a separation of phases in the solid state; the resulting two-phase structure is formed by aggregates or domains of hard segments dispersed in the elastomeric matrix of the soft segment.

Hard segments, dispersed in a matrix of soft segments, act as reinforcing particles and behave as physical cross-linking sites, which are reversible at high temperatures, giving the material elastomeric characteristics. Further, these materials can undergo typical processing of the polymeric materials; once cooled they behave again as chemically cross-linked rubbers.

The driving force for the segregation in domains is the chemical incompatibility between the soft and hard segments. Factors affecting the phase separation grade include intermolecular hydrogen bond, copolymer composition, solubility of hard segments with respect to soft segments, crystallizability of each of the two segments, manufacturing method and thermal and mechanical history.

The presence of a high number of hydrogen bonds is a typical characteristic of polyurethanes. Recent studies (Wilkes, J. A.; Emerson, J. Applied Phys. 47, 4261 (1976); W. Seymour, G:M: Estes, S. L. Cooper, Macromolecules, 3, 579, (1970)) stressed out that the separation grade affects the quantity and the type of hydrogen bond, not the contrary; the higher is the separation, the higher is the quantity of interurethane hydrogen bonds that forms.

Biomedical application of thermoplastic polyurethanes

Polyurethanes have found wide use in the creation of short term biomedical devices (catheters, endotracheal tubes, cannulas), but also for the production of permanent implants (intraaortic balloons, artificial ventricles, vascular prostheses) because they have good mechanical properties, very good abrasion and flexing resistance, good bio- and haemocompatibility, they are self-lubricating and easily processible.

Synthesis of thermoplastic segment-polyurethanes

The most important reaction for the synthesis of polyurethanes is the addition on the C=N bond. The reaction advances with a nucleophilic attack on the carbon atom of the isocyanate group by an alcohol, with formation of a urethane group —NH—CO—O—. The synthesis of polyurethanes is based on reactions occurring between the isocyanate group (—NCO) and a nucleophilic group (NH or OH) present in many compounds such as for example amines and alcohols. In the case of amines, urea bonds are formed (NH—CO—NH) and poly-urea-urethanes are so obtained.

Cross-linked polyurethanes are obtained by using at least a reactant having functionality higher than two, typically a triol or a tetraol. Linear polyurethanes are obtained starting from polydiols and bifunctional isocyanates.

Thermoplastic segment-polyurethanes can be prepared with two different procedures:

a single step process, with a direct reaction between diisocyanate and diol (and/or diamine)

a two-step process, more used than the former in biomedical field: in a first step diisocyanate and polyol are reacted, forming a prepolymer, subsequently the obtained macromonomer is reacted with the chain extender, whereby a high molecular weight polymer is produced.

During the polymerisation, also the following unwanted side reactions can occur (J. H. Saunders, K. C. Frisch, Polyurethanes Chemistry and Technology, Interscience Publishers):

reaction between diisocyanate and water, leading to the formation of an amine with release of carbon dioxide reaction between diisocyanate and urethane groups, leading to the formation of allophanates (cross-linking). It occurs particularly at high temperatures reaction between diisocyanate and ureic groups, thus forming biurets reaction between aromatic diisocyanates (in particular conditions), forming dimers reaction between aliphatic or aromatic diisocyanates, giving trimers.

The most used catalysts are tertiary amines or organometallic compounds, in particular those containing tin (Brunette, S: L: Hsu, W: J. Macknight, Macromolecules, 15, 71, (1982).

Tin organometallic compounds specifically catalyse the reaction between isocyanate and hydroxyl; accordingly they should be preferred to the amines for the production of elastomeric polyurethanes. Both tertiary amines and tin-organometallic compounds are cytotoxic (M. C. Tanzi, P. Verderio, Lampugnani et al., "Cytotoxicity of some catalysts commonly used in the synthesis of copolymers for biomedical use", J. Mat. Science: Mats. In Medic., 5, (1994)). It is therefore necessary to carry out a careful purification after the synthesis of the copolymer if its use in biomedical field is foreseen.

Diisocyanates

The most commonly used diisocyanates are the aromatic ones, in particular 2,4-toluendiisocyanate (TDI) and 4,4'-methylene-bis-phenyldiisocyanate (MDI).

The use of aliphatic diisocyanates, among which 1,6-hexamethylenediisocyanate (HDI), trans-1,4-cyclohexyldiisocyanate (CHDI), 4,4'-methylene-bis-cyclohexyldiisocyanate (HMDI) (the hydrogenated analogous of MDI), is less common.

Polyurethanes obtained from aromatic diisocyanates tend to form intermolecular bonds stronger than those formed between polyurethanes obtained with aliphatic diisocyanates (Stokes, J. Biomat. Appls. 3, 248 (1988) M. Szycher, J. Biomater. Appl., 3, 383 (1988)), showing a higher aptitude to the semicrystalline form. On the contrary, hard segments containing aliphatic diisocyanates not always have the possibility to crystallise, in fact, both HMDI and CHDI have different conformational isomers, which perturb crystallinity of the hard segments.

Since more crystalline hard segments help more phase separation in the copolymer, mechanical properties of aromatic polyurethanes are better than those of aliphatic polyurethanes; moreover the aromatic compounds are more reactive than the aliphatic ones, allowing to use lower doses of or eliminating the catalyst during the synthesis.

The advantage given by aliphatic diisocyanates is that the obtained polyurethanes do not become yellow, when exposed to light. The unwanted phenomenon of yellowing, occurring when aromatic diisocyanates are used, can be prevented by adding antioxidant agents, which must be however avoided in the case of implantable devices.

In-vivo studies (Stokes, J. Biomat. Appls. 3, 248 (1988); M. Szycher, J. Biomater. Appl., 3, 383 (1988)) demonstrated the relative stability of aromatic polyurethanes with respect to the aliphatic ones. (Christ, S. Y. Buchen, D. A. Fencil, P. Knight, K. D. Solomon and D. J. Apple, J. Biomed. Mat. Res., 26, 607 (1992)). Further, aromatic polyurethanes show a better flex fatigue.

The cancerogenic activity of possible release products, coming from aromatic polyurethanes, is still an unsolved problem. At the present state of the art, it is not sure that aromatic polyurethanes release carcinogenic substances in man; however part of the scientific research is investigating the possibility to obtain aliphatic polyurethanes with improved mechanical properties.

Macroglycols: polyester, polyether, polycarbonate

Polyester and polyether diols are the most commonly used macroglycols for the synthesis of polyurethanes for biomedical applications, in particular polytetramethylene oxide), even if recently new types of macroglycols with higher biostability, such as polycarbonate diol (Pinchuk "A review of the biostability and carcinogenity of polyurethanes in medicine and a new generation of 'biostable' polyurethanes" J. Biomat. Sci. Polymer Edn., 6, (3), 225–267 (1994), M. Szycher et al. "Biostable polyurethane elastomerics", Medical Device Technology, 11, (1992), 42–51); polyethers with a higher number of CH2 groups between oxygen bridges (G. F. Meijs et Al., "Polyurethane elastomerics containing novel macrodiols I. Synthesis and properties", Trans. 4th World Biomaterials Congress, 1992, 473) and aliphatic macroglycols (A. J. Coury et Al., "Novel soft segment approaches to implantable biostable polyurethanes", Trans. 4th World Biomaterials Congress, 1992, 661) have been studied and developed. The necessity of using different macroglycols is determined by the fact that polyurethanes obtained from polyester diols or polyether diols are subjected to in-vivo degradation and this effect is determined just by the type of glycol (Stokes, P., Urbanski, K., Cabian "Polyurethanes in Biomedical Engineering, p. 109, H. Plank et al., (eds) Elsevier, Amsterdam 109 (1987), (Pinchuk "A review of the biostability and carcinogenity of polyurethanes in medicine and a new generation of 'biostable' polyurethanes" J. Biomat. Sci. Polymer Edn., 6, (3), 225–267 (1994).

Polyesterurethanes suffer self-catalytic acid hydrolytic degradation (or basic, but it is an uncommon situation in physiological environment) (Amin, J. Willie, K, Shah, A. Kydonieus, J. Biomed. Mat. Res., 27, 655 (1993)), in the presence of acids, enzymes (esterases) and oxidants.

Thorough studies were carried out on the degradation of polyetherurethanes, which are hydrolytically much more stable than polyesterurethanes and are used in long term applications (W. Hergenrother, H. D. Wabers, S. L. Cooper "Effect of hard segment chemistry and strain on the stability of polyurethanes: in vivo stability", Biomat., 14, 449 (1993)).

The polyether leading to a polyurethane with the best physical properties is PTMO (or PTMEG). Polyetherurethanes prepared with this soft segment present a mechanical strength comparable to the one of polyesterurethanes and very good hydrolytic stability (D.

Lelah, S. L. Cooper, Polyurethanes in Medicine, p. 27–28, CRC Press (1986)). In the past, hydrogenated polybutadiene and polyisobutylene were also used as macroglycols, allowing the synthesis of polyurethanes with excellent resistance to light, thermal and hydrolytic degradation (Brunette, C. M. Hsu, S. L. Macnight, W. J., and Schnider, "Structural and mechanical properties of polybutadiene-containing polyurethanes", Polym. Eng. Sci., 21, 163, (1981)). Unfortunately, the synthesis of these materials is difficult and the physical properties of the resulting polymer are lower than the ones of conventional polyurethanes.

Chain extenders: diols or diamines

Chain extenders used for the production of polyurethanes with a biphasic structure and desirable physical properties have a low molecular weight with respect to macrodiisocyanate and when they react with it, they are included in the hard segment, increasing the chain molecular weight. It was demonstrated that when the chain of the extender contains an even number of carbon atoms, the hard segment crystallises easier than when the number of carbon atoms is odd, such as in the case of nylons. Generally a more rigid crystalline domain brings to a polyurethane with better physical characteristics (D. Lelah, S. L. Cooper, Polyurethanes in Medicine, p. 27–28, CRC Press (1986). Chain extenders are bifunctional and end with amino or hydroxy groups, giving rise to polyureaurethanes and polyurethanes, respectively, characterised by a different morphology and by different mechanical properties. Diamines form urea bonds, which make polyureaurethanes less soluble in the common solvents and make them more difficult to process in melting processes, such as extrusion or moulding, thus limiting their application in the production of fibres and coatings (dip-coating). Moreover, recent studies have demonstrated that polyetherureaurethanes are more sensitive to biodegradation with respect to the analogous polyetherurethane containing butandiol as chain extender (Pinchuk "A review of the biostability and carcinogenity of polyurethanes in medicine and a new generation of 'biostable' polyurethanes" J. Biomat. Sci. Polymer Edn., 6, (3), 225–267 (1994)). Advantageously, polyureaurethanes, since they have stronger intermolecular bonds, have a higher fatigue resistance.

Polyurethaneamides (PUA) are poorly disclosed in literature.

Copolymers obtained from macroglycols, having diisocyanates and dicarboxylic acids as chain extenders, are an example of PUA. In this case, in the second reaction step CO2 develops, with formation of amide bonds (D. Cohn, A. Penhafi, Clinical Materials, 8, p. 105 (1991).

The tendency demonstrated by amido groups to form strong intermolecular hydrogen bonds leads to the formation of well distinct hard domains, giving the polymeric material improved mechanical properties. Further, rigidity and planarity increase, combined with amido groups, itself contributing to develop a sharper phase separation with consequent better mechanical properties, is an advantageous characteristic of these chain extenders.

For these reasons, the need to have available new polyurethaneamides using diols containing amido groups as chain extenders is still present. Said extenders, not commercially available, must be purposely synthesised.

SUMMARY OF THE INVENTION

It has now surprisingly been found that the compound of formula

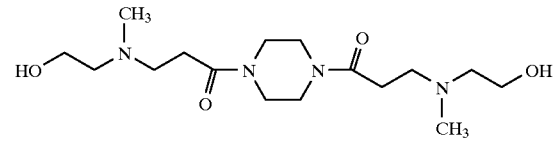

is a very good chain extender for heparinizable polymers, in particular elastomerics, and more in particular polyurethanes.

The compound according to the invention (in the following named PIME, for brevity) gives the obtained polymers the desired mechanical and physico-chemical properties required to the materials for the manufacture of biocompatible, implantable devices.

It is an object of the present invention the compound named PIME, a process for its preparation, its use as chain extender for the preparation of polymers.

According to the invention, the polymers (meaning both omopolymers and copolymers, both linear and cross-linked) containing PIME as chain extender and in any way obtainable by using the compound PIME as chain extender, are a further object of this invention. In particular, the complexes between said polymers and heparin are still a further object of this invention.

Another object of the present invention are materials and articles comprising the above polymers and/or their complexes with heparin, in particular biocompatible materials and articles which come into contact with blood and/or are implantable.

DETAILED DESCRIPTION OF THE INVENTION

Figure 1:
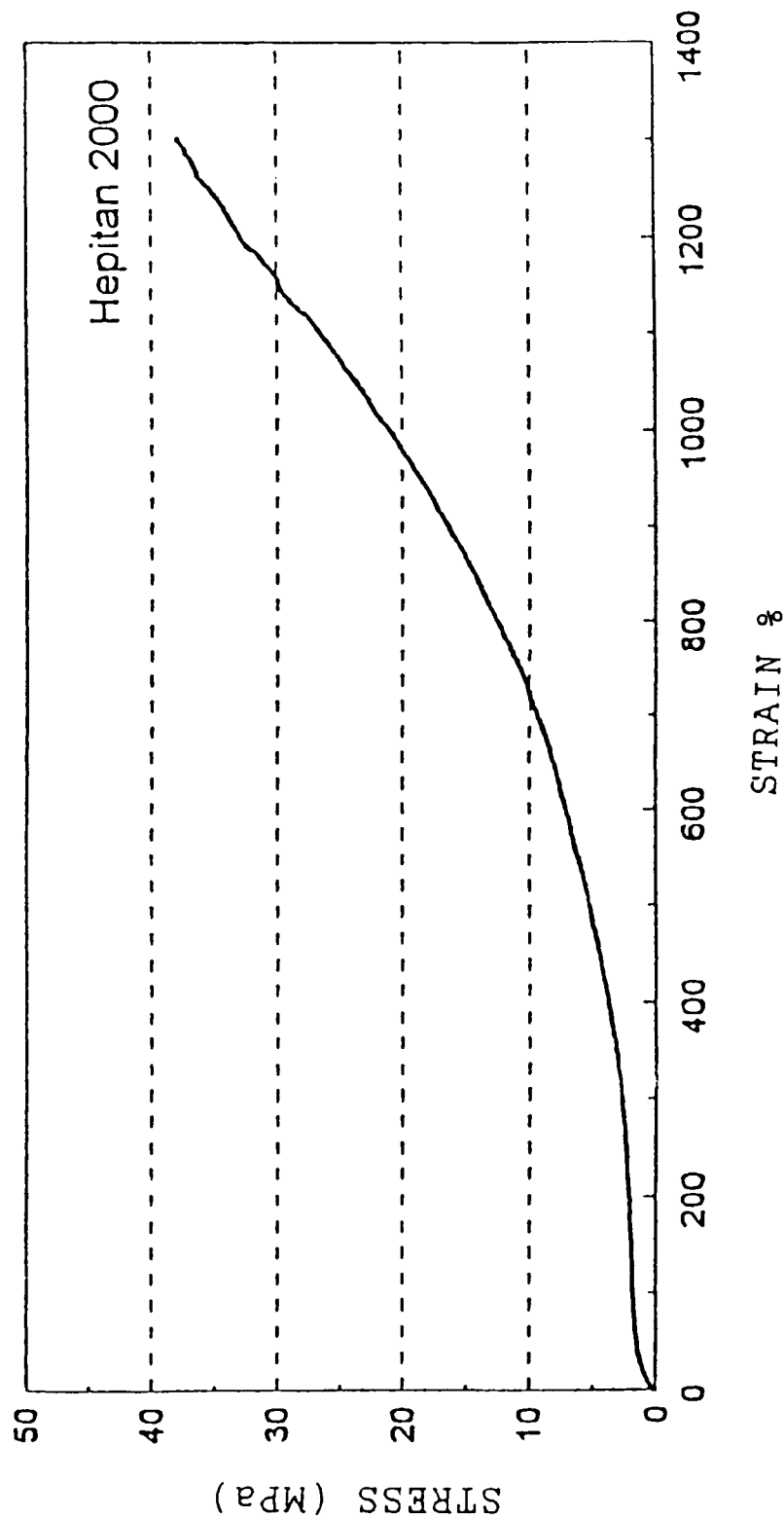
FIG. 1 provides a stress/strain curve (mechanical tensile test) for an embodiment of the present invention.

The compound PIME is prepared by reacting 1,4-bisacryloyl-piperazine with N-methyl-ethanol amine, both of them being commercially available products.

The preparation is made following conventional procedures that the skilled person well knows. Preferably, the molar ratio between 1,4-bisacryloyl-piperazine and N-methyl-ethanol amine is 1:2. Usually the reaction is performed in an appropriate solvent, at such a temperature that the reaction can take place in an appropriate period of time without creating by-products or decomposition products under an uncontrolled way. Preferably, the temperature is included in the range of 10 and 50° C., for a period lasting from some hours to some days. Isolation and purification of the final product are performed with usual and known methods, i.e. by precipitating and, when necessary, further purifying the product.

The use of the compound PIME as chain extender in the preparation of polymers does not require any particular procedure, but the usual polymerisation techniques.

In a first preferred realisation of the invention, the polymer is a polyurethane. Especially preferred the polyurethane is prepared with an aliphatic diisocyanate, e.g. 1,6-hexamethylene diisocyanate, and a macroglycol, selected among those conventionally known. The conditions of the reaction are known and described in the pertaining literature. Therefore, temperature, pressure, solvents and catalysts are easily determined as a function of the desired polymer type.

PIME can be used as chain extender for polymers of biomedical interest, e.g., besides the polyurethanes, the polyesters.

Polymers obtainable by using PIME as chain extender can be used for the preparation of biomedical items to be used in contact with blood, to be implanted or not, such as for example circuits for extra-corporeal circulation and dialysis, catheters, probes, cardiovascular prostheses, an artificial ventricle in particular. Such polymers can be used for surface coating of other materials or devices in order to improve their haemocompatibility.

Such polymers and devices and materials that incorporate them are heparinizable that is they form complexes with heparin, and such complexes are inside the present invention.

The following examples further illustrate the present invention.

EXAMPLE 1

Synthesis of PIME

To a solution prepared by dissolving at room temperature under magnetic stirring 3 g of 1,4-bisacryloyl-piperazine (BISPIP, 15.4 mmol) in methanol (21 ml), 2.3 g of N-methyl-ethanol amine (MEA, 30.9 mmol) are added. The syringe used to add MEA is then washed with=10 ml of methanol that is added to the reaction mixture.

The reaction is allowed to take place at room temperature and in the dark for 3 days, always under stirring.

The reaction mixture is concentrated to ¼ of the original volume with a rotating evaporator under reduced pressure and at 55° C.

The product is then precipitated into 100 ml diethylether and recovered by filtration. The filtrated powder is then washed three times with 50 ml diethylether each and dried under vacuum at 40° C.

5.6 g of a white powder are obtained (yield =99%).

Characterisation

Elemental analysis: found % c 55.66; % h 9.40M % n 16.08 (calculated % C 55.79; % H 9.36; % N 16.27)

Titration of the amino groups:

0.5 g of PIME, dried to constant weight for 12 h in oven at 40° C. under vacuum, is dissolved into distilled water and titrated with HCl 0.1N.

0.4075 g are titrated with 24.6 ml HCl 0.096N, corresponding to a 99.3% purity. The point of colour change has been determined with an Orion mod. SA 720 pHmeter. The determination of the colour change was made by the differential method.

Titration of alcoholic groups

Potassium dichromate ($K_2Cr_2O7$) is desiccated in oven at 150–200° C. for 2 h. After cooling down, a 0.1N aqueous solution is prepared.

A 0.1N solution of Mohr salt (hexahydrated ammonic ferrous sulphate, $Fe(NH_4)_2 * 6H_2O$) is prepared and titrated with the $K_2Cr_2O_7$ solution.

As titration indicator a solution of ferroin is used, prepared by dissolving 1.485 g of o-phenantroline and 0.695 g of ferrous sulphate in 100 ml water.

0.35 g of vacuum dried PIME is dissolved in water and 100 ml of $K_2Cr_2O_7$ solution are added. The pH is lowered with concentrated sulphuric acid to pH<2. After stirring for a few minutes, 3 drops of ferroine are added and the excess of $K_2Cr_2O_7$ is titrated with the Mohr salt solution.

The resulting purity is 98.8%.

Thin layer chromatography (TLC)

A mixture of ethanol: chloroform: ammonium hydroxide in the ratio 10 ml: 5 ml: 30 drops was used as eluant. TLC plates, with 0.2 mm thick silica gel on aluminium support were used. TLC were developed by exposing to iodine vapours. Retention factor is $R_f$ PIME=0.158.

Hiqh performance liquid chromatography (HPLC)

Instrument: Bio-Rad Chr. System, equipped with a Value Chrom™ Chromatography Software; columns: Bio-Gel TSK-30+TSK-40 (Bio-Gel); detector: UV, λ=220 nm.

Phosphate buffer (0.1 M $Na_2SO_4$, 0.02 M $NaH_2PO_4$ pH=6.8) as eluant was used, at a flow rate of 1 ml/min.

The sample of PIME is solubilized in the same buffer (0.2% w/v) and injected. The chromatogram points out the presence of a single peak (retention time: 19.55 min).

Fourier-Transformed Infrared Spectroscopy (FT-IR)

Transmission infrared spectroscopy analysis (IR) was performed with a Fourier-transformed spectrometer FT 1710 Perkin Elmer.

The sample was directly deposited onto the KBr crystal by solvent casting from acetone solution. Table 1 reports the main absorptions and their attributions.

TABLE 1

| Frequency (cm$^{-1}$) | Attribution |
| --- | --- |
| 3500–3300 | Stretching of OH |
| 3000–2880 | Symmetric and asymmetric stretching of —CH$_2$ |
| 2815–22780 | Symmetric stretching of —CH$_3$ and of N—CH$_3$ |
| 2820 | Stretching of amine —N—C—H |
| 1650–1600 | Stretching of amido C=0 |
| 1500–1350 | Bending of —CH$_2$ |
| 1370–1310 | Stretching of tertiary aliphatic amine >N—CH$_3$ |
| 1300–1150 | Stretching of tertiary amide C—N |
| 1230–1030 | Stretching of tertiary aliphatic amine C—N |

$^1$H-NMR

An 80 MHz instrument was used. The sample was dissolved in CDCl$_3$, and the reference was TMS.

In table 2 values and attributions of the signals are reported.

TABLE 2

| Chemical shift (ppm)* | Integration | Attribution |
| --- | --- | --- |
| 2.2 ppm (S) | 6H | N—CH$_3$ |
| 2.4–2.9 ppm (m) | 12H | CH$_2$ |
| 3.2 ppm (s)** | 2H | OH |
| 3.4–3.7 ppm (m) | 12H | CH$_2$ |

*s = singlet; m = multiplet;
**exchange with D$_2$O

DSC

DSC analyses were recorded with a differential calorimeter Mettler TA3000 instrument, previously calibrated with an indium standard. The sample of 7–9 mg weight was heated at a rate of 20° C./min under nitrogen, in the temperature range from −50° C. to +180° C. A melting peak was observed at 110.5° C. (ΔH=197.9 J/g).

Solubility tests

PIME is soluble at room temperature in methanol, water, chloroform, and methylene chloride, dimethylacetamide (concentration 10 mg/ml); insoluble in diethylether at room temperature.

Hygroscopicity 0.4231 g of PIME desiccated to constant weight in oven at 40° C. under vacuum are left in the air (relative humidity= 67%) and weighed every 10'. After 1 h the sample reaches the weight of 0.4293 (weight % gain=1.47)

Cytotoxicity tests

Cytotoxicity of PIME has been evaluated towards human endothelial cells (HEC).

Cell cultures

HEC were isolated from human umbilical vein by treatment with 0.1% collagenase and cultured to confluence into plastic culture wells in medium 199 containing 20% foetal calf serum, 50 mg/ml endothelial cell growth supplement, 50 mg/ml heparin, 50 U/ml penicillin, 50 mg/ml streptomycin, 2.5 mg/ml fungizone. as described in literature (E. Dejana, M. G. Lampugnani, J.Cell.Biol., 109, 367–375 (1989)).

Evaluation of cell adhesion and growth

HEC suspensions were seeded in tissue culture microplates of 96 well, 0.28 cm$^2$, (4×10$^3$ cells/well). After 4 h incubation, adhesion was verified, the medium was replaced with fresh one containing different PIME concentrations (1, 0.1 or 0.01% w/v). All the tests were made in triplicate. As controls, adhesion and growth values in wells containing only the culture medium were used.

Evaluation of cells growth was carried out stopping the experiment after 40 and 72 h from seeding; non-adherent cells were removed by twice washing with Ca$^{++}$ and Mg$^{++}$ free PBS, fixed and stained with crystal violet. Optical density was then read at 560 nm with an automatic photometer Tirtrek. By this way, the cells viability was evaluated, being directly related to the colour intensity.

Table 3 shows the values for the control sample at increasing times

TABLE 3

| Time | Optical density at 560 nm |
| --- | --- |
| 4 h | 0.055 ± 0.007 |
| 40 h | 0.108 ± 0.009 |
| 72 h | 0.181 ± 0.012* |

*optical density value corresponding to the confluence of the cell layer

The wells containing PIME, in every concentration tested, gave optical density values identical or slightly higher than the control. From these results it can be deduced that PIME shows a very good compatibility with the cell growth.

EXAMPLE 2

The use of PIME as chain extender

The reaction takes place in two steps. In the first step the diisocyanate (1,6-hexamethylene diisocyanate, HDI) reacts with the macroglycol giving the macrodiisocyanate; the reaction is catalysed by dibutyltin-dilaurate (DBTDL). In the second step the addition of the chain extender to the macrodiisocyanate occurs, creating high molecular weight linear chains. The stoichiometric ratio of the reagents macroglycol:diisocyanate:extender was 1:2:1.

By using three different macroglycols (polytetramethylene glycol having molecular weight of 2000 and 1000, poly (1,6-hexyl 1,2-ethyl carbonate) diol and the same diisocyanate and chain extender three copolymers were synthesised, named in the following Hepitan 2000, Hepitan 1000 and Hepitan CA.

Copolymers Hepitan 1000 and Hepitan 2000 are obtained with polytetramethylene glycol (PTMG) having molecular weight of 1000 and 2000, respectively. From poly (1,6-hexyl 1,2-ethyl carbonate diol) (CA) the copolymer Hepitan CA is prepared.

Preparation of reagents and synthesis of the polymer

The macroglycol was desiccated under reduced pressure at 90° C. for 24 h; the chain extender was desiccated at 60° C. under reduced pressure for 14 h. The solvent of the reaction (DMAC, N, N'-dimethylacetamide) was distilled under reduced pressure and kept over molecular sieves.

A solution of HDI (1.61 g; 10 mmol) and catalyst (0.1 g) is prepared under inert atmosphere, at 65° C., under stirring. The macroglycol (5 mmol) dissolved into 25 ml DMAC is added dropwise. The mixture is allowed to react for 90 min at 65° C. (the reaction time was estimated by titration of the isocyanate groups). The reaction mixture is then precipitated into deionized water and the precipitate is washed twice with water, each washing lasting two hours. The product is desiccated under reduced pressure at 40° C. until constant weight.

Titration of the isocyanate groups

The titration of unreacted —NCO groups was carried out on samples withdrawn from the reaction mixture at different reaction times. The method of the analysis follows the guidelines of ASTM D2572-70 standard practice, according to which a sample of the reaction mixture is reacted with an excess of N-dibutyl amine, according to the following reaction:

$$(C_4H_9)_2NH + R\text{—}NCO => (C_4H_9)_2NH\text{—}CO\text{—}NH\text{—}R$$

At the end of this reaction, the excess of N-dibutyl amine is determined by inverse titration with HCl of known titre.

A sample of about 1 g weight is taken from the reaction mixture, weighed with a technical scale. Dilution is made with 25 ml of DMAC.

5 ml of 0.05M N-dibutyl amine in DMAC is added with a burette, the solution is stirred for 15 minutes.

Titration is performed with 0.05N HCl, using blue of bromophenol as indicator. Blank titration is performed separately.

The percentage of non-reacted —NCO is calculated as follow:

$$\% \text{ --NCO} = \frac{\text{titrated NCO moles}}{\text{theoretical NCO moles}} \times 100$$

Theoretical —NCO moles present in the sample taken from the reaction mixture are:

$$\text{Theoretical --NCO moles} = \frac{\text{HDI moles} \times 2 \times W}{\text{reaction mixture weight}}$$

where W is the weight of the sample.

Moles of —NCO which have reacted with N-dibutyl amine are:

$$\text{titrated NCO moles} = V(HCl) \times M(HCl)$$

The reaction mixture is regularly sampled until the —NCO content is constant. From these data, the reaction can be considered ended after 5 h from the addition of the macroglycol to the solution containing the diisocyanate and catalyst.

Purification from the catalyst

A 15% solution of the copolymer in dimethylacetamide at 40° C. is prepared. The solution is washed three times with equal volume of petroleum ether in a separatory funnel.

Residual tin content, evaluated by inductively coupled plasma emission spectrophotometry (ICP), is $\leq 50$ ppm.

Calculation of hard segment percentage

Considering that hard segment is composed of the diisocyanate and the chain extender, the weight per cent of hard segments (% $S_h$) is calculated as follows:

$$S_h = \frac{\text{hard molar mass}}{\text{polyurethane molar mass}} \times 100 = \frac{2 \times \text{MHDI} + \text{MPIME}}{2 \times \text{MHDI} + \text{MGLYCOL} + \text{MPIME}} \times 100$$

$S_h$ values are reported in table 4.

TABLE 4

| | % $S_h$ |
|---|---|
| Hepitan 2000 | 25.3 |
| Hepitan 1000 | 40.5 |
| Hepitan CA | 29 |

Characterisation is performed by viscosimetry, gel permeation chromatography (GPC), Fourier transformed infrared spectroscopy (FT-IR), differential scanning calorimetry (DSC), and mechanical tensile tests. Solubility tests of the copolymers were also performed.

Solubility tests

Solubility of the purified copolymer, at a concentration of 0.5% w/w, was checked. The copolymer was cut into pieces of about 3×2×0.7 mm and put in each of the selected solvent. It was left for 24 h under stirring at room temperature. A identical solution was then prepared, letting it at a temperature ranging between 40° C. and 50° C., until a maximum time of 6 h.

The copolymers were soluble at room temperature in dimethylacetamide, dimethylformamide, and tetrahydrofuran; insoluble in acetone, 2-butanone, methanol, ethanol, petroleum ether, diethyl ether, and hexane. Soluble in ethanol and methanol at 45° C.

Intrinsic viscosity measurements

A capillary viscometer in a thermostatic bath (Haake DC3) at 40° C. was used. The sample was dissolved into dimethylacetamide at a concentration of 1 g/dl. Results are reported in Table 5.

TABLE 5

| | [η] |
|---|---|
| Hepitan 2000 | 0.91 |
| Hepitan 1000 | 0.98 |
| Hepitan CA | 0.90 |

Size exclusion liquid chromatography (GPC)

The analyses have been performed with a Waters GPC instrument (pump, column thermostat, refraction index detector, thermostat, integrator) equipped with a set of four columns in series: Shodex AD 802/S, AD 804/S, KD 803, AD 80 M/S. As eluant, dimethylformamide HPLC grade at 40° C. and at a flow rate of 1 ml/min was used.

The calibration curve, obtained with a kit of polymethylmethacrylate standard samples (Polymer Laboratories), had a coefficient of linear regression higher than 0.99. All the samples were filtered before the analyses.

All polyurethanes showed $M_w$ and $M_n$ values in agreement with data reported in literature, having dispersion indexes comprised between 1.5 and 2.5. An example: Hepitan 2000 shows $M_w$=257.000, $M_n$=173.000 (d=1.48).

FT-IR

The transmission infrared spectroscopic analyses were performed with a Fourier transformed infrared spectrometer FT 1710 Perkin Elmer. Samples were circular films of 3 cm diameter obtained by solvent casting from 0.5% w/v DMAC solutions.

The infrared spectrum confirmed the expected structure for the copolymers.

Differential Scanning Calorimetry (DSC)

A differential Scanning Calorimeter Mettler TA 3000 was used, with indium for calibration.

The sample (10–16 mg weight) was cooled at −150° C. and subsequently heated to 300° C. at a flow rate of 20° C./min under dry nitrogen (nitrogen flow rate=50 cm$^3$/min).

Table 6 reports data for thermal transitions in the copolymers.

TABLE 6

|  | Tg | Tm (° C.) (Δ H/ J/g) | Tmll (° C.) (Δ H J/l) |
|---|---|---|---|
| Hepitan 2000 | −72 | 14.5 (29.7) | 270 (20.1) |
| Hepitan CA | −68 | 23.2 (56.5) | 234 (4) |

Mechanical Tensile tests

Mechanical tensile tests on Hepitan 2000 have been performed at a deformation rate of 20 mm/min at 250° C. with a Instron dynamometer model 4301 having a 1 kN load cell and connected with a PC, allowing the control and programming of the apparatus with a software supplied by the manufacturer (Instron series XII).

The sample sheets were prepared by solvent casting from a 15–20% w/v solution in DMAC. The solution was cast into 8×5 cm rectangular dies made of glass (about 3.5 g of polymer in each cast), and then maintained at 40° C. under reduced pressure for 48–72 h. The obtained sheets had a thickness of 0.5–1 mm.

From the sheets, with a manually operated cutter, specimens having size and form according to ASTM D-638 Standard Practice, which provides the use of at least 5 dog-bone specimens, were obtained.

The stress/strain curves show the typical trend of polyurethane elastomerics (see FIG. 1). Following an initial increase of the modulus until the yield point, the material shows a relaxation, with a decrease of the elastic modulus, which then increases again until break.

Stability tests

Tests of structural stability were carried out for Hepitan 2000 in deionized water (21 days at 37° C.) and buffered saline solution, PBS (25 days at 37° C.). As reference, two commercial polyurethanes, a polyetherurethane (Pellethane 2363 80AE) and a polycarbonateurethane (corethane) were selected.

To evaluate the presence of products released from the materials, GP-HPLC analyses of contacting solutions were performed after 25 days in PBS and 14/21 days in H$_2$O.

Two samples for each material, having a rectangular shape of 10×20 mm, with a thickness ranging from 0.3 to 0.5 mm, were desiccated in a vacuum oven at 40° C. for 16 h (until constant weight), before and after incubation with H$_2$O and PBS. The samples were cut from sheets obtained by solvent casting.

Stability in H$_2$O at 37° C. (21 days)

The samples were immersed into glass tubes containing 20 ml of deionized water.

After 14 days immersion, a HPLC analysis of the water in contact with the samples was performed. After having replaced this water with a fresh one, the samples were left at 37° C. for an additional week. This water was analysed by HPLC too. The samples were then weighed, after having been dried in a vacuum oven at 40° C. for 16 h.

The results are reported in Table 7

TABLE 7

Stability in H$_2$O at 37° C. for 21 days

|  | weight loss (mg) | weight loss (%) |
|---|---|---|
| HEPITAN 2000 | 0–0.3 | 0.18 |
| CORETHANE 80A | 0–0.1 | 0.06 |
| PELLETHANE | 0–0.2 | 0.08 |

After 21 days immersion into deionized water at 37° C., a per cent weight loss <1% was observed for the analysed polyurethanes.

The chromatographic analysis of water in contact for 14 days with the materials shows only not significant traces of released substances. Moreover, chromatography of the second contacting water evidenced that no substances were released from the samples.

Stability in PBS at 37° C. (25 days)

The samples were immersed into 20 ml glass tubes containing PBS (phosphate buffered saline solution, pH=7.4), prepared by dissolving a tablet of phosphate buffer into 200 ml of deionized water. 0.02% sodium azide was added to prevent bacterial growth. The tubes were placed in oven at 37° C. for 25 days.

After this time, as shown in Table 8, a per cent weight loss <1% was observed for the considered polyurethanes.

TABLE 8

Stability in H$_2$O at 37° C. for 21 days

|  | weight loss (mg) | weight loss (%) |
|---|---|---|
| HEPITAN 2000 | 0.8–1 | 0.72 |
| CORETHANE 80A | 0.3–0.2 | 0.24 |
| PELLETHANE | 0.4–0.8 | 0.52 |

Heparin binding properties by the copolymers

The ability of binding heparin stably by Hepitan 2000 copolymer was evaluated with $^{125}$I labelled heparin, in comparison with two commercially available biomedical polyurethanes (Pellethane 2363 80AE, and Corethane 80A). The kinetic versus time of the binding between heparin and polyurethanes was evaluated. Then, the subsequent release of adsorbed heparin was checked in physiological buffer solution (PBS), alkaline solution (NaOH 1M) and detergent solution (SDS 2%), in the order. The amount of released heparin has been measured by gamma radiation counter (COBRA II AUTO-GAMMA (Camberra Packard)).

Heparin labelling

Heparin was reacted with the Bolton-Hunter reactive (Thrombosis Research, 14, 845–860 (1979)) (SHPP: succinimidyl hydroxyphenyl propionate), which has an aromatic ring capable of binding $^{125}$I isotope. A gel filtration was carried out in order to purify the derivatized heparin from the unreacted reactive. The amount of labelled heparin was evaluated by a calorimetric method.

Experimental procedure 5.3 mg of heparin were reacted with an excess of succinimidyl hydroxyphenyl propionate (SHPP (5.3 mg)) in 5 ml of 0.05M sodium borate (pH 9.2) at 4° C. for 20 h. The unreacted SHPP excess was hydrolysed into acid and separated by gel filtration in water on a PD-10 column (Pharmacia) filled with a previously equilibrated Sephadex G-25 M.

Radio-iodination was carried out by incubating at room temperature a solution of heparin and Na$^{125}$I in a glass tube coated with Iodogen (1,3,4,6-tetrachloro-3a,6a-diphenyl glycoluryl, used as oxidative reagent). Free $^{125}$I is separated from labelled heparin through a G-25 resin column. The amount of $^{125}$I present in the eluant was measured by gamma counter.

Kinetic versus time

Disks (5 mm diameter, 0.5 mm thickness) were cut from film obtained by solvent casting. Tests were made in duplicate for every test time.

Samples were preincubated in PBS+0.02% NaN$_3$ for 2 days; subsequently, PBS+NaN$_3$ is substituted and the labelled heparin (60 ml, 150 mg, corresponding to 50000 cpm) is added. The amount of bonded heparin was evaluated after 30', 60', 2 h, 4 h, 6 h, 24 h. After each incubation time, the samples were washed twice with PBS+NaN$_3$ and dried before counting radioactivity.

Figure 2:
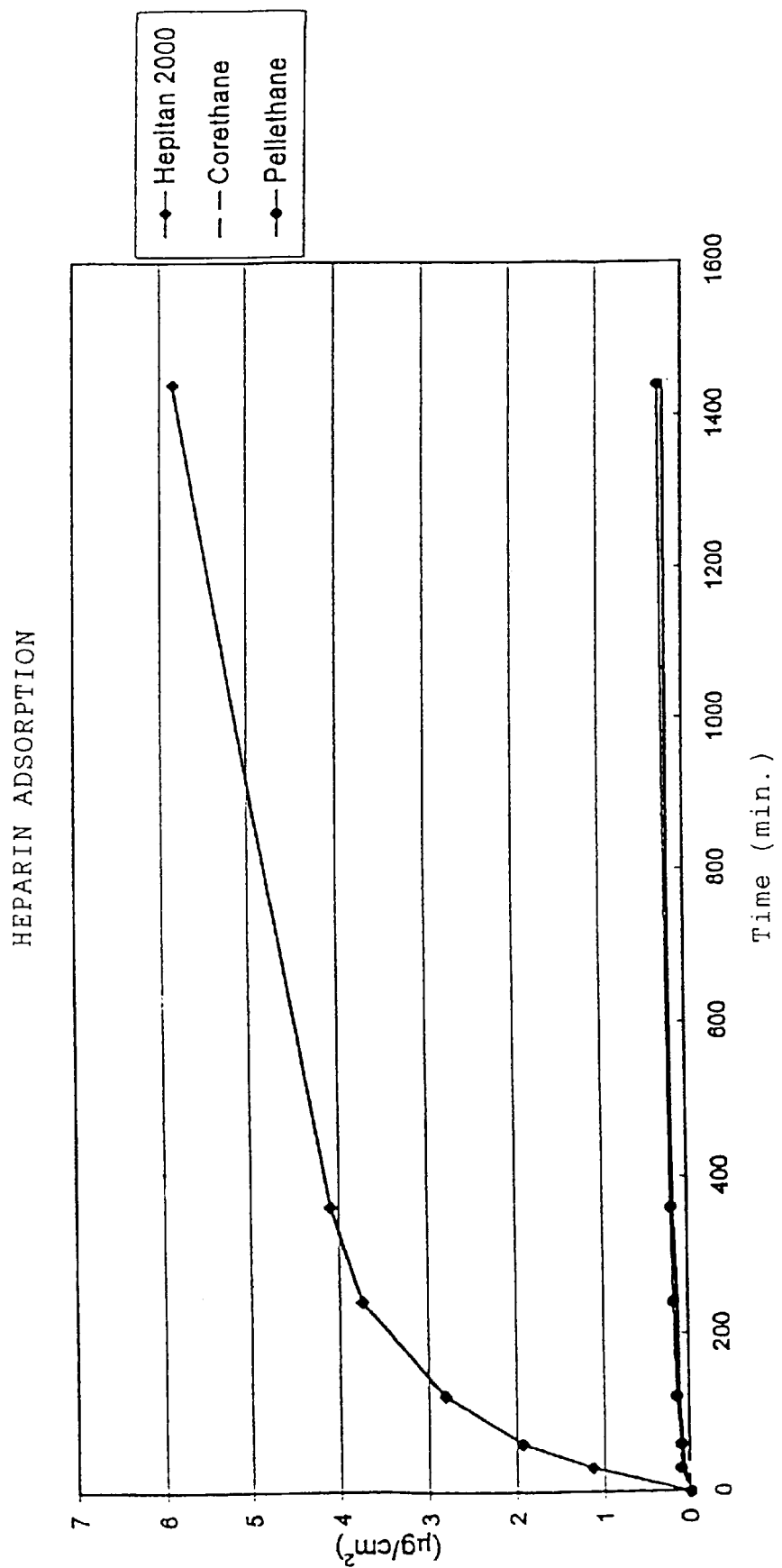
FIG. 2 compares heparin absorption rates of an embodiment of the present invention and prior art compositions.

In FIG. 2 obtained results are plotted: time is reported in minutes along the abscissas, while the amount of absorbed heparin in mg/cm$^2$ is reported on the ordinates. Values were calculated considering that heparin is bonded at the surface of the sample, which is calculated considering the two faces of the disk and the lateral surface.

Release

The samples that had been incubated with heparin for 6 h were repeatedly washed with PBS to evaluate the amount of adsorbed, but not stably bonded, heparin. Subsequently, these samples were washed with 1M NaOH, in order to evaluate the amount of electrostatically bonded heparin. Finally, they were washed with a detergent solution (2% SDS).

Figure 3:
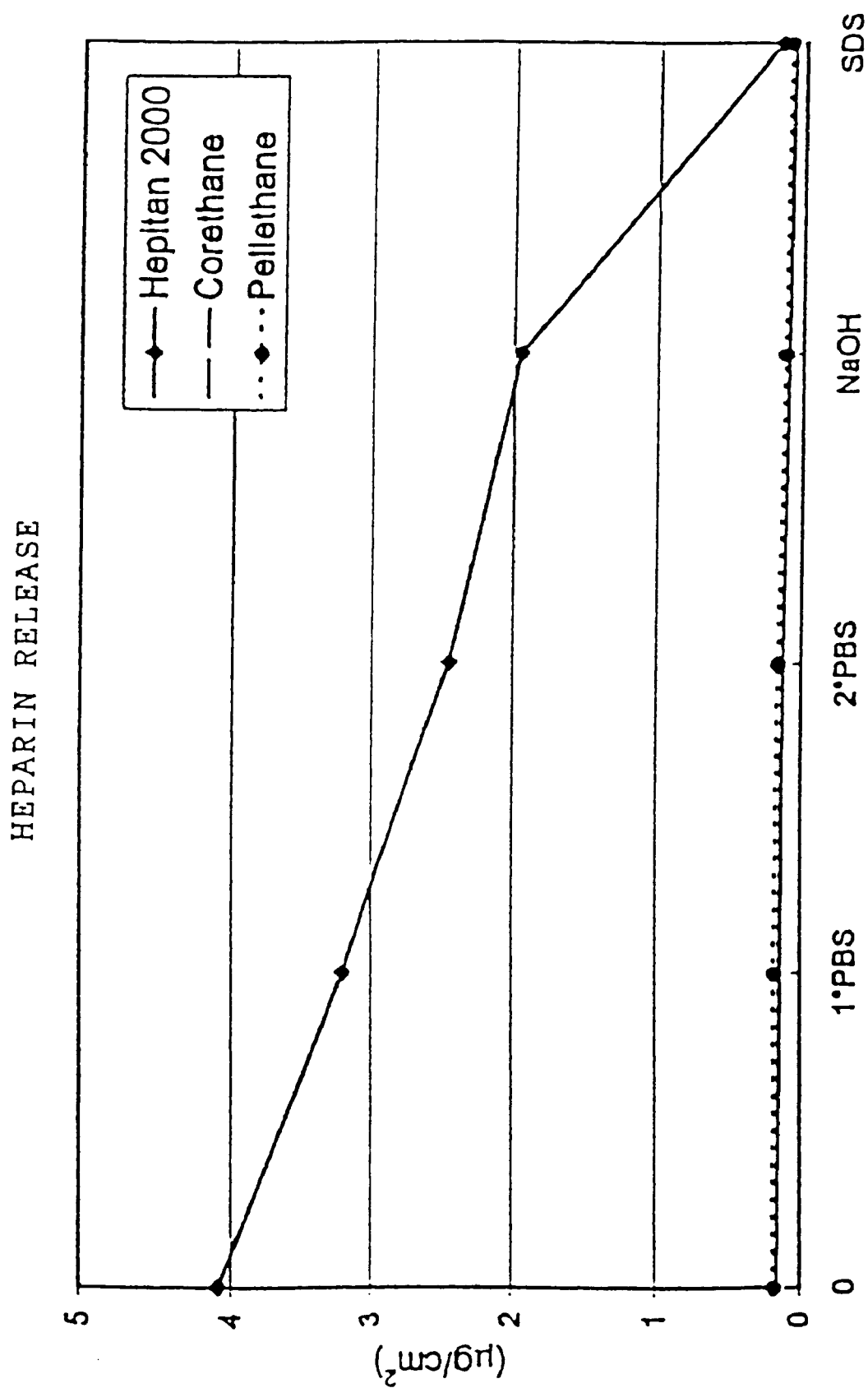
FIG. 3 compares heparin release profiles of an embodiment of the present invention and prior art compositions.

In particular, these washing steps were carried out:

2 washings with PBS for 24 h 1 washing with 1M NaOH for 24 h 1 washing with 2% SDS (sodium dodecylsulphate) for 48 h Experimental results are reported in FIG. 3.

Results

Hepitan 2000 shows a far higher ability of binding heparin, if compared to the commercial polyurethanes, for which heparin binding is almost zero. For Hepitan, the amount of bonded heparin grows quickly in the first part of the kinetic curve, after 6 h the curve reaches almost a plateau. Observing the plot of heparin release it is possible to draw the conclusion that heparin is very stably bonded on Hepitan 2000: in fact, the release is slow and incomplete for the washings with in PBS and NaOH, but it is necessary to use a detergent in order to achieve the total release.

From these data one can conclude that the bond type between Hepitan 2000 and heparin seems to be not exclusively of the ionic type, as the washing with NaOH 1M does not give the total release of bound heparin. Hydrophobic interactions (which are eliminated with a detergent, such as SDS), are likely to occur together with the ionic bond.

I claim:

1. In a process for preparing a polyurethane polymer, the improvement which comprises incorporating into said polymer as a chain extender the compound 1,4-bis-{β-[N-methyl-N-(2-hydroxyethyl)amino]propionyl}piperazine.

2. A process for preparing a thermoplastic polyurethane block copolymer which comprises a) reacting a diisocyanate with a polyol to form a prepolymer, and b) reacting said prepolymer with 1,4-bis-{β-[N-methyl-N-(2-hydroxyethyl)amino]propionyl}piperazine to form said thermoplastic polyurethane block copolymer.

3. The process of claim 2, wherein said diisocyanate is 1,6-hexamethylene diisocyanate and said polyol is a macroglycol.

4. The process of claim 2, wherein said macroglycol is a polytetramethylene glycol having a molecular weight of 2000.

5. The process of claim 3, wherein said macroglycol is a polytetramethylene glycol having a molecular weight of 1000.

6. The process of claim 3, wherein said macroglycol is a poly(1,6-hexyl-1,2-ethylcarbonate)diol.

7. A polyurethane polymer containing 1,4-bis-{β-[N-methyl-N-(2-hydroxyethyl)amino]propionyl}piperazine as a chain extender.

8. A polymer obtained by the process of claim 2.

9. A complex of heparin and a polymer of claim 8.

10. Biomaterials comprising a polymer of claim 8 and being selected from the group consisting of circuits for extra-corporeal circulation and dialysis, catheters, probes, and cardiovascular protheses.

11. An article surface coated with a polymer of claim 8.

12. Heparinized material comprising a complex of claim 9.

13. Cardiovascular prostheses comprising a polymer of claim 8.

14. A biomedical article intended to be in contact with blood, whether implantable or not, comprising a polymer of claim 8.

15. A biomedical article intended to be in contact with blood, whether implantable or not, comprising a complex of claim 9.

* * * * *